(12) United States Patent
Rondoni et al.

(10) Patent No.: US 8,193,766 B2
(45) Date of Patent: Jun. 5, 2012

(54) TIME REMAINING TO CHARGE AN IMPLANTABLE MEDICAL DEVICE, CHARGER INDICATOR, SYSTEM AND METHOD THEREFORE

(75) Inventors: John C. Rondoni, Plymouth, MN (US); Jon P. Davis, St. Michael, MN (US); Kevin L. Bright, Maple Grove, MN (US); Rajeev M. Sahasrabudhe, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 848 days.

(21) Appl. No.: 12/112,344

(22) Filed: Apr. 30, 2008

(65) Prior Publication Data

US 2009/0273318 A1    Nov. 5, 2009

(51) Int. Cl.
*H02J 7/00* (2006.01)
*A61N 7/00* (2006.01)

(52) U.S. Cl. ........ 320/108; 320/125; 320/124; 320/133; 320/137; 607/61

(58) Field of Classification Search .................. 320/107, 320/108, 132, 103, 109, 114, 115, 112, 113, 320/124, 125, 127, 128, 133, 137, 134, 135, 320/136, 160, 161, 162, 155; 607/61
See application file for complete search history.

(56) References Cited

U.S. PATENT DOCUMENTS

| | | | |
|---|---|---|---|
| 4,949,046 A | 8/1990 | Seyfang | |
| 4,952,862 A | 8/1990 | Biagetti et al. | |
| 5,185,566 A | 2/1993 | Goedken et al. | |
| 5,349,540 A | 9/1994 | Birkle et al. | |
| 5,411,537 A * | 5/1995 | Munshi et al. | 607/33 |
| 5,690,685 A * | 11/1997 | Kroll et al. | 607/5 |
| 5,723,971 A | 3/1998 | Sakai et al. | |
| 5,789,900 A | 8/1998 | Hasegawa et al. | |
| 6,169,387 B1 * | 1/2001 | Kaib | 320/132 |
| 6,198,253 B1 | 3/2001 | Kurle et al. | |
| 6,278,258 B1 * | 8/2001 | Echarri et al. | 320/130 |
| 6,329,793 B1 | 12/2001 | Bertness et al. | |
| 6,516,227 B1 | 2/2003 | Meadows et al. | |

(Continued)

FOREIGN PATENT DOCUMENTS

EP    1 048 324 A2    11/2000

(Continued)

OTHER PUBLICATIONS

International Search Report for PCT/US2009/031625.

*Primary Examiner* — Edward Tso
*Assistant Examiner* — Alexis Boateng
(74) *Attorney, Agent, or Firm* — IPLM Group, P.A.

(57) ABSTRACT

System and method for estimating a time to recharge a rechargeable power source of an implantable medical device. A plurality of measured parameters relating to the implantable medical device and an external charging device are applied to a model of recharging performance and an estimate is provided to a patient, perhaps in advance of charging. Once charging has begun, updated estimates can be provided until charging is complete. Once charging is complete, the model may be updated to reflect any differences in the estimated time to complete charging and the actual time required to complete charging. The model may be based on limitations to the rate at which charge may be transferred to the rechargeable power source over a plurality of intervals.

11 Claims, 9 Drawing Sheets

U.S. PATENT DOCUMENTS

| | | | |
|---|---|---|---|
| 6,553,263 B1* | 4/2003 | Meadows et al. | 607/61 |
| 6,842,460 B1 | 1/2005 | Olkkonen et al. | |
| 6,892,148 B2 | 5/2005 | Barsoukov et al. | |
| 6,928,372 B2 | 8/2005 | Pozsgay et al. | |
| 7,109,684 B2* | 9/2006 | Takaoka et al. | 320/132 |
| 7,245,107 B2 | 7/2007 | Moore et al. | |
| 7,248,929 B2* | 7/2007 | Meadows et al. | 607/61 |
| 7,317,947 B2* | 1/2008 | Wahlstrand et al. | 607/61 |
| 7,813,801 B2* | 10/2010 | Youker et al. | 607/29 |
| 7,865,245 B2* | 1/2011 | Torgerson et al. | 607/61 |
| 7,881,796 B2* | 2/2011 | Scott et al. | 607/36 |
| 2002/0140399 A1* | 10/2002 | Echarri et al. | 320/130 |
| 2003/0085684 A1* | 5/2003 | Tsukamoto et al. | 320/108 |
| 2003/0114899 A1* | 6/2003 | Woods et al. | 607/60 |
| 2004/0017180 A1 | 1/2004 | Cook | |
| 2004/0162592 A1 | 8/2004 | Betzold et al. | |
| 2004/0220758 A1 | 11/2004 | Barsoukov et al. | |
| 2005/0004619 A1 | 1/2005 | Wahlstrand et al. | |
| 2005/0075693 A1* | 4/2005 | Toy et al. | 607/60 |
| 2005/0110466 A1* | 5/2005 | Shoji | 320/150 |
| 2005/0277994 A1* | 12/2005 | McNamee et al. | 607/29 |
| 2007/0063683 A1 | 3/2007 | Coq et al. | |
| 2007/0069687 A1* | 3/2007 | Suzuki | 320/108 |
| 2007/0090790 A1* | 4/2007 | Hui | 320/108 |
| 2007/0156205 A1* | 7/2007 | Larson et al. | 607/61 |
| 2007/0257636 A1* | 11/2007 | Phillips et al. | 320/108 |
| 2008/0097544 A1 | 4/2008 | Gandhi et al. | |
| 2008/0258679 A1* | 10/2008 | Manico et al. | 320/106 |
| 2009/0163820 A1* | 6/2009 | Eerden | 600/481 |

FOREIGN PATENT DOCUMENTS

| | | |
|---|---|---|
| EP | 1 610 437 A1 | 12/2005 |
| JP | 2006 046919 A | 2/2006 |
| WO | WO01/08749 A1 | 2/2001 |
| WO | WO01/34243 A1 | 5/2001 |
| WO | WO 2008/038202 A1 | 4/2008 |
| WO | WO2008/038202 A2 | 4/2008 |

* cited by examiner

TIME REMAINING TO CHARGE AN IMPLANTABLE MEDICAL DEVICE, CHARGER INDICATOR, SYSTEM AND METHOD THEREFORE

FIELD

The present invention relates generally controllers, systems and methods for implantable medical devices and, more particularly, to such controllers, systems and methods for managing the recharging of rechargeable power sources associated with implantable medical devices.

BACKGROUND

The medical device industry produces a wide variety of electronic devices for treating patient medical conditions. Depending upon the medical condition, medical devices can be surgically implanted or connected externally to the patient receiving treatment. Medical professionals or other clinicians use medical devices alone or in combination with drug therapies and surgery to treat patient medical conditions. For some medical conditions, medical devices provide the best, and sometimes the only, therapy to restore an individual to a more healthful condition and a fuller life. Examples of implantable medical devices designed to deliver therapeutic electrical stimulation include neurological stimulators, pacemakers, defibrillators and drug pumps. Most implantable medical devices are powered by an internal battery or other power source associated with or internal to the device.

Because surgery is required to implant most implantable medical devices, it is desirable, particularly in devices that consume power quickly, to make the internal battery rechargeable. An external power source may then be used to recharge the rechargeable battery, commonly transcutaneously via an inductive link between an external coil and an internal coil. Depending on the nature of the implantable medical device and rechargeable battery in question, several hours will commonly be required to fully recharge the rechargeable battery. While some implantable medical devices may be able to delivery therapy to a patient for months or years on a single charge of a primary, non-rechargeable battery, some devices, particularly those that rely on a rechargeable power source or that deliver a relatively large amount of therapy constantly, may consume most of their charge in a matter of days or weeks.

Commonly, in order to recharge their implantable medical device, patients may sit in close proximity of their external charger, maintaining a recharging head, or the entire device, nearby or within a few inches of their implantable medical device. The rechargeable battery will commonly require several hours to charge from a relatively low amount of charge to a full or nearly-full level of charge. It is known in the art to provide patients with information pertaining to an estimated time to fully charge a rechargeable battery.

U.S. Pat. No. 6,928,372, Pozsgay et al., discloses a method for determining time to completion for a battery charging system. The system preferably includes a charger having a microprocessor and a battery with a memory. The memory includes information about the battery, including battery identifiers, charging state, charging procedures and charging termination information. The charger reads this battery and then determines the charging states associated with the battery. The charger then determines the present state of charge and calculates a time to completion for that state. The charger then determines times to completion for the remaining charge states, optionally compensating for self discharge within the battery. A total time to completion is determined by summing the times to completion for the respective charging states.

SUMMARY

But the recharging of the rechargeable power source of an implantable medical device may involve factors neither contemplated nor compensated for in the prior art that relates to external power sources. In a system utilizing inductive energy transfers, the closer the inductive coils are to each other, and the better the orientation of the coils to each other, the stronger the inductive field becomes resulting in an ability to transfer more energy per unit time. For certain patients, it may not be possible or practical to obtain a consistent transfer of energy to the implantable medical device both during a recharging session and from session to session. For instance, the patient has to position and then hold in place the external charger. To whatever extent the external charger moves during a charging session or after a charging session, the amount of energy that may transfer per unit time may vary. Further, over time physiological changes in the patient, such as a buildup of fatty tissue between the patient's skin and the implantable medical device, may further increase the distance between the external charger and the implantable medical device, thereby further altering the effectiveness of the inductive connection and varying the amount of time needed to recharge the rechargeable power source.

But where the model for how much time is required to recharge a rechargeable power source to does not adapt to reflect variances in the ability to transfer energy per unit time, the estimates for how much time will be required to recharge may be consistently inaccurate for different patients. It has been determined that patients may be consistent in the manner in which they position their external charger relative to their implantable medical device, with only periodic or gradual changes in the manner in which they position the external charger. Further, physiologic changes may tend to be relatively gradual. As such, a system has been developed that adapts the model for estimating the time to complete a recharge of a rechargeable power source for an implantable medical device. After making a timing estimate based on a predetermined model and then conducing the recharge session, the estimated time may be compared against the actual time that was required to recharge. Based on the difference between the estimated and the actual times, the model that was utilized to generate the estimated time may be modified to reflect actual performance. When the model is consistently updated, changes in the habits of the patient for how their external charger is positioned, as well as physiological changes, may be automatically factored in to the recharge model, resulting in timing estimates that are consistently more accurate for each patient.

A system has been developed that estimates a time to complete a recharging session. The estimate may be made and displayed to the patient before recharging begins. In addition, ongoing estimates may be provided to the patient during recharging in order to keep the patient up to date as to how long they should expect the session to last. In order to accomplish these estimates, a model for how recharging sessions commonly proceed has been developed, and may be utilized to make the estimate based on a plurality of measured parameters. However, the model may not be able to anticipate recharging performance for all implantable medical devices under all circumstances. Thus, for each implantable medical device and for each patient the model can be updated by comparing the estimate of how recharging will proceed with how recharging actually proceeded. Thus, as time passes, estimates for how long recharging will take will tend to become progressively more accurate and reliable.

In an embodiment, a system comprises an implantable medical device having a rechargeable power source, the rechargeable power source having a charge level and a charge capacity. The system further comprises an external charger operatively coupled to the implantable medical device, the external charger having an external power source, the external charger charging the rechargeable power source, electronic componentry determining an estimated time until the charge level reaches a predetermined level following commencement of a recharge session based on a plurality of measured parameters and a predetermined recharge model, and a user output operatively coupled to the external charger and to the electronic componentry, outputting the time to a user. The predetermined recharge model is updated based on an actual time to recharge compared with the estimated time.

In an embodiment, the external charger further comprises a primary coil, wherein the implantable medical device further comprises a secondary coil, and wherein the external charger operatively couples to the implantable medical device when the primary coil is placed in proximity of the secondary coil.

In an embodiment, the plurality of measured parameters comprise at least one of: voltage over the primary coil; current through the primary coil; voltage over the external power source; voltage over the implantable power source; current through the implantable power source; voltage over the secondary coil; current through the secondary coil; temperature; charge stored in the external power source; charge capacity of the external power source; temperature of the external charger; and temperature of the implantable medical device.

In an embodiment, the electronic componentry further determines a plurality of charging rates based on the plurality of measured parameters and the recharge model.

In an embodiment, the predetermined recharge model has a plurality of intervals, each individual one of the plurality of intervals having an individual one of a plurality of limiting factors, the plurality of charging rates being based, at least in part, on at least one of the plurality of limiting factors.

In an embodiment, the electronic componentry determines the time further based on the lowest individual one of the plurality of charging rates for each of the plurality of intervals.

In an alternative embodiment, the system comprises an implantable medical device having a rechargeable power source, the rechargeable power source having a charge level and a charge capacity, and an external charger. The external charger has an external power source operatively coupled to the implantable medical device and charging the rechargeable power source, an electronic componentry, and a user output operatively coupled to the external device and to the electronic componentry, outputting the time to a user. The electronic componentry determines an estimated time until the charge level reaches a predetermined level following commencement of a charge session by determining a plurality of charging rates based on a plurality of measured parameters and a predetermined recharge model, the predetermined recharging model having a plurality of intervals, each individual one of the plurality of intervals having an individual one of a plurality of limiting factors, the plurality of charging rates being based, at least in part, on at least one of the plurality of limiting factors, wherein the charging of the rechargeable power source occurs at a lowest individual one of the plurality of charging rates. The predetermined recharge model is updated based on an actual time to recharge compared with the estimated time.

In an embodiment, a method determines an estimated time to charge an implantable medical device having a rechargeable power source, the rechargeable power source having a charge level and a charge capacity and being operatively coupled to an external charger. The method comprises the steps of determining the estimated time until the charge level reaches a predetermined level following commencement of a recharge session based on a plurality of measured parameters and a predetermined recharge model, charging the rechargeable power source using the external charger, wherein the determining step occurs during the charging step, outputting the estimated time to a user, and updating the predetermined recharge model based on an actual time to recharge compared with the estimated time.

In an embodiment, the method further comprises the step of determining a plurality of charging rates based on the plurality of measured parameters and the recharge model.

In an embodiment, the predetermined recharge model has a plurality of intervals, each individual one of the plurality of intervals having an individual one of a plurality of limiting factors, the plurality of charging rates being based, at least in part, on at least one of the plurality of limiting factors.

In an embodiment, the determining step is further based on the lowest individual one of the plurality of charging rates for each of the plurality of intervals.

In an alternative embodiment, a method determines an estimated time to charge an implantable medical device having a rechargeable power source, the rechargeable power source having a charge level and a charge capacity, the rechargeable power source being operatively coupled to an external charger. The method comprises the steps of charging the rechargeable power source using the external charger at a lowest individual one of a plurality of charging rates determined by a plurality of measured parameters and a predetermined recharge model, wherein the predetermined recharge model has a plurality of intervals, each individual one of the plurality of intervals having an individual one of a plurality of limiting factors, the plurality of charging rates being based, at least in part, on at least one of the plurality of limiting factors, determining the estimated time until the charge level reaches a predetermined level following commencement of a recharge session based on the plurality of measured parameters and the predetermined recharge model, outputting the estimated time to a user, and updating the predetermined recharge model based on an actual time to recharge compared with the estimated time.

DESCRIPTION

In order to maximize the efficiency and effectiveness of recharging sessions of implantable medical devices equipped with rechargeable power sources, it is desirable to provide patients with information relating to the recharging session. Accurate information may help the patient to better plan for, and to conduct, recharging sessions. Patients may want to know how long it will take to recharge their implantable medical device, which would better help them fit a recharging session into their schedules. Unfortunately, it is often difficult for a patient or other user to determine how long a recharging session may last. The amount of time a recharging session may take is dependent on a variety of factors and parameters which have not previously been well understood by a typical patient.

In an embodiment, a system has been developed that determines an estimated time until the charge level of a rechargeable power source of an implantable medical device reaches a desired level during a recharge session and outputs that estimated time to the patient or other user. The system obtains a plurality of parameters relating to the components of the implantable medical device and external charger and applies those parameters to a model of the system to arrive at the estimated time. The model takes into account that at different times during a recharging session different factors will limit how fast the transfer of charge from the external charger to the implantable medical device may occur. Initially, the model used may be the same for every implantable device of a given type. However, the model may be updated depending on the accuracy of the initial estimate compared with the actual time a recharging required. Thus, the model for any given implantable medical device may become increasingly customized to the particular implantable medical device and the behaviors and habits of the patient in whom the implantable medical device has been implanted.

Figure 1:
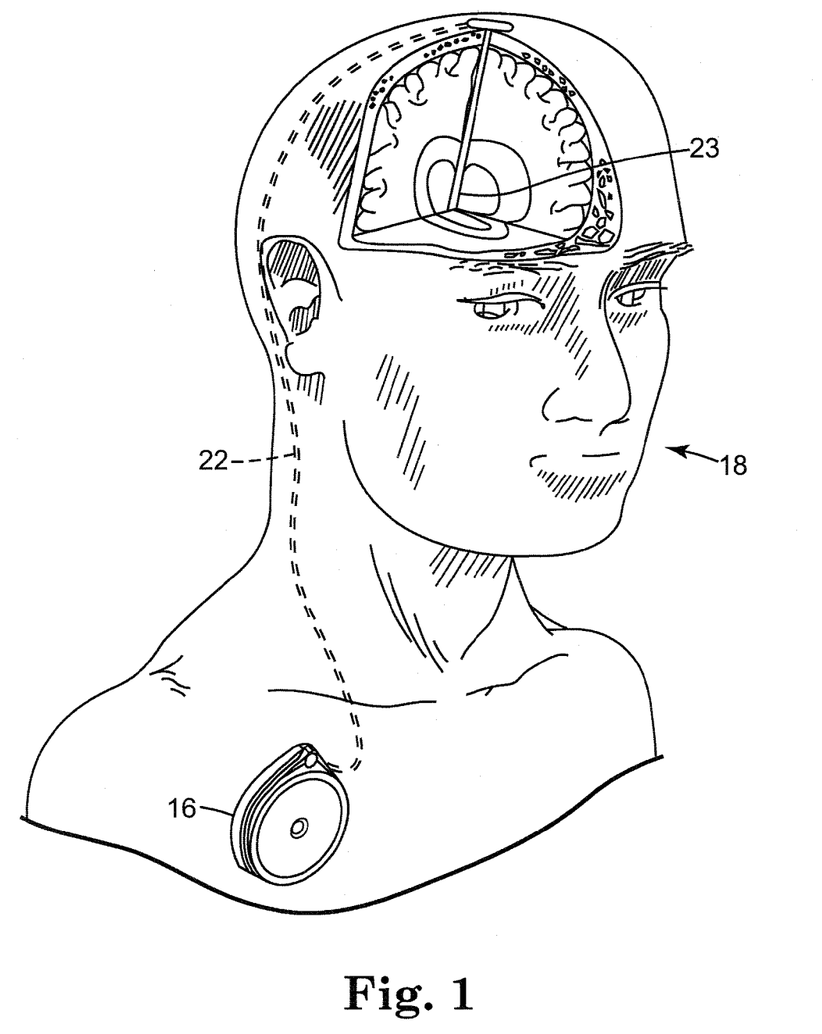
FIG. 1 shows an example of an implantable medical device, e.g. a neurological stimulator, implanted, with electrodes positioned leading into the patient's brain.

Use of an external power source having an antenna with a plurality of concentric primary coils can generally be illustrated by the generic system in FIG. 1, which shows implantable medical device 16, for example, a neurological stimulator, implanted in patient 18. The implantable medical device 16 is typically implanted by a surgeon in a sterile surgical procedure performed under local, regional, or general anesthesia. Before implanting the medical device 16, a lead 22 is typically implanted with the distal end position at a desired therapeutic delivery site 23 and the proximal end tunneled under the skin to the location where the medical device 16 is to be implanted. Implantable medical device 16 is generally implanted subcutaneously at depths, depending upon application and device 16, of from 1 centimeter (0.4 inches) to 2.5 centimeters (1 inch) where there is sufficient tissue to support the implanted system. Once medical device 16 is implanted into the patient 18, the incision can be sutured closed and medical device 16 can begin operation.

Implantable medical device 16 can be any of a number of medical devices such as an implantable therapeutic substance delivery device, implantable drug pump, electrical neurological stimulator, cardiac pacemaker, cardioverter or defibrillator, as examples.

If implantable medical device 16 is a drug infusion device, for example, implantable medical device 16 operates to infuse a therapeutic substance into patient 18. If implantable medical device 16 is a neurological stimulator, implantable medical device 16 operates to electrically stimulate tissue in patient 18 in order to obtain a physiologic response. Implantable medical device 16 can be used for a wide variety of therapies such as pain, spasticity, cancer, and many other medical conditions.

The therapeutic substance contained in implantable medical device 16 is a substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances may or may not be intended to have a therapeutic effect and are not easily classified such as saline solution, fluoroscopy agents, disease diagnostic agents and the like. Unless otherwise noted in the following paragraphs, a drug is synonymous with any therapeutic, diagnostic, or other substance that is delivered by the implantable infusion device.

Figure 2:
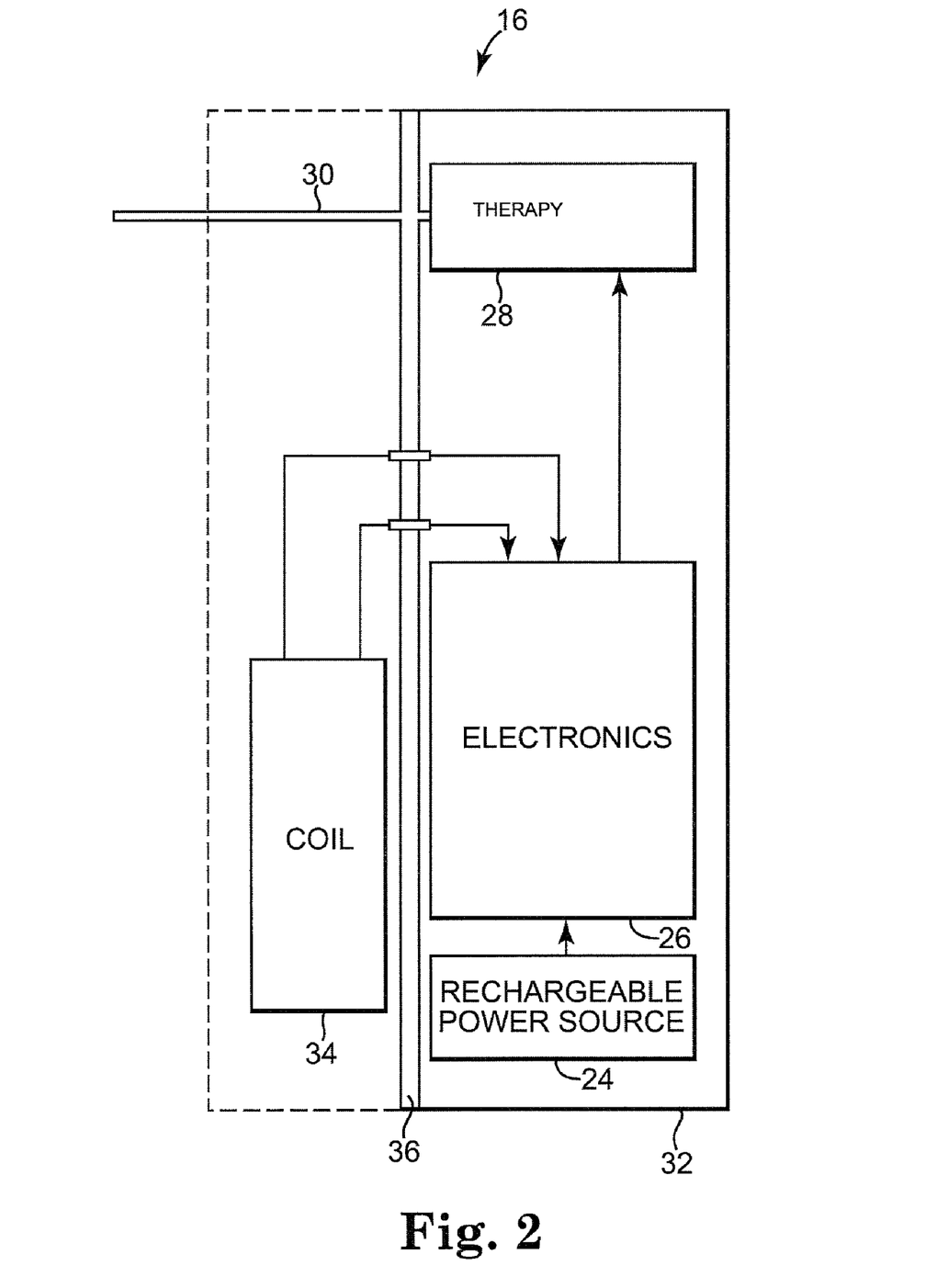
FIG. 2 shows an exemplary block diagram of an implantable neurological stimulator of FIG. 1.

If implantable medical device 16 is an electrical stimulator, for example, therapy module 28 may deliver an electrical stimulus, such as an electrical pulse, or series of electrical pulses, either mono-polar or bi-polar, through one or more electrical leads and/or electrodes to provide specific or general benefit to that patient such as pain relief or muscular control.

In FIG. 2, implantable medical device 16 has a rechargeable power source 24, such as a Lithium ion battery, powering electronics 26 and therapy module 28 in a conventional manner. Alternatively, coil 34, rechargeable power source 24, or both, may be located outside of housing 32. Therapy module 28 is coupled to patient 18 through one or more therapy connections 30, also conventionally. Rechargeable power source 24, electronics 26 and therapy module 28 are contained in hermetically sealed housing 32. Secondary charging coil 34 is attached to the exterior of housing 32. Secondary charging coil 34 is operatively coupled through electronics 26 to rechargeable power source 24. In an alternative embodiment, secondary charging coil 34 could be contained in housing 32 or could be contained in a separate housing umbilically connected to electronics 26. Electronics 26 help provide control of the charging rate of rechargeable power source 24 in a conventional manner. Magnetic shield 36 is positioned between secondary charging coil 34 and housing 32 in order to protect rechargeable power source 24, electronics 26 and therapy module 28 from electromagnetic energy when secondary charging coil 34 is utilized to charge rechargeable power source 24.

Rechargeable power source 24 can be any of a variety power sources including a chemically based battery or a capacitor. Rechargeable power source may be a well known lithium ion battery.

Figure 3:
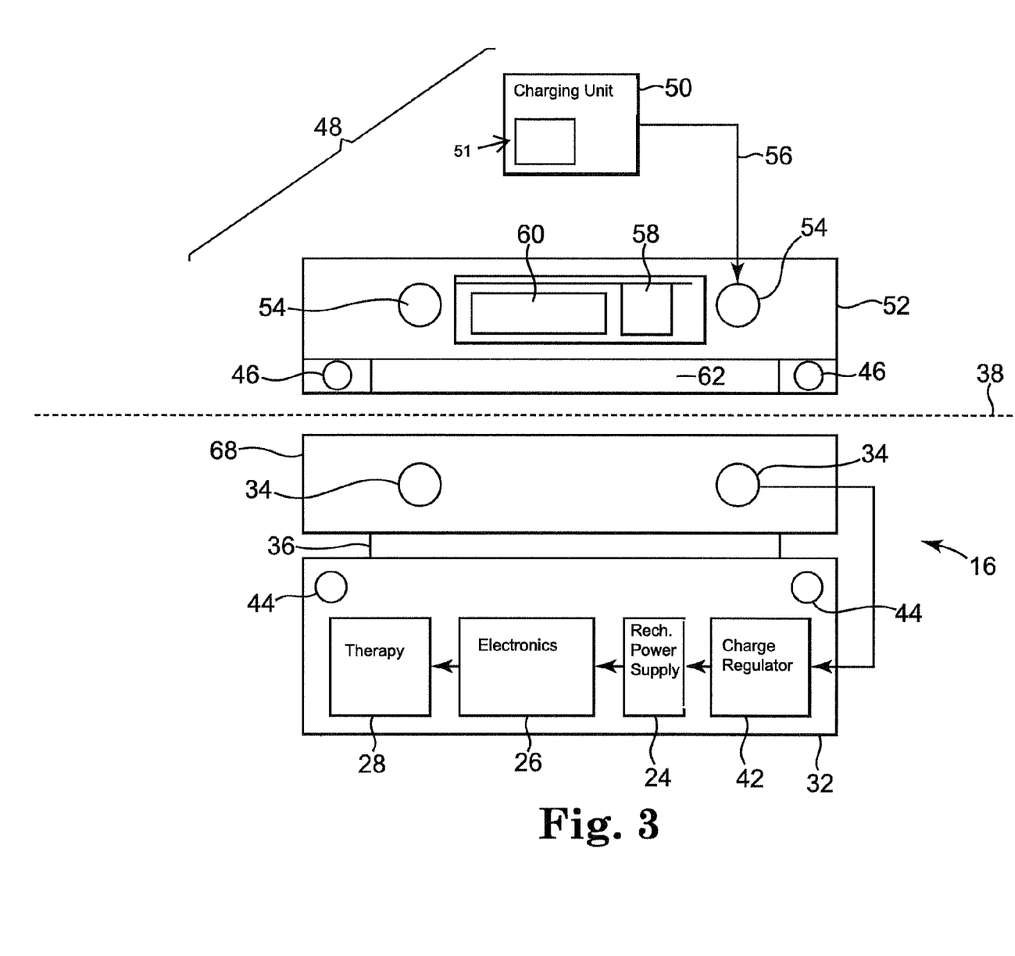
FIG. 3 shows a more descriptive block diagram of the implantable neurological stimulator of FIG. 2 and a block diagram of an external charging device.

FIG. 3 illustrates an alternative embodiment of implantable medical device 16 situated under cutaneous boundary 38. Implantable medical device 16 is similar to the embodiment illustrated in FIG. 2. However, charging regulation module 42 is shown separate from electronics 26 controlling therapy module 28. Again, charging regulation and therapy control is conventional. Implantable medical device 16 also has internal telemetry coil 44 configured in conventional manner to communicate through external telemetry coil 46 to an external programming device (not shown), charging unit 50 or other device in a conventional manner in order to both program and control implantable medical device 16 and to externally obtain information from implantable medical device 16 once implantable medical device 16 has been implanted. Internal telemetry coil 44, rectangular in shape with dimensions of 1.85 inches (4.7 centimeters) by 1.89 inches (4.8 centimeters) constructed from 150 turns of 43 AWG wire, is sized to be larger than the diameter of secondary charging coil 34. Secondary coil 34 is constructed with 182 turns of 30 AWG wire with an inside diameter of 0.72 inches (1.83 centimeters) and an outside diameter of 1.43 inches (3.63 centimeters) with a height of 0.075 inches (0.19 centimeters). Magnetic shield 36 is positioned between secondary charging coil 34 and housing 32 and sized to cover the footprint of secondary charging coil 34.

Internal telemetry coil 44, having a larger diameter than secondary coil 34, is not completely covered by magnetic shield 36 allowing implantable medical device 16 to communicate with the external programming device with internal telemetry coil 44 in spite of the presence of magnetic shield 36.

It is to be recognized and understood that internal telemetry coil 44 and secondary charging coil 34 could, in some circumstances be one and the same coil, a single coil essentially doing double duty as internal telemetry coil 44 at some time and as secondary charging coil 34 at another time. It is also to be recognized and understood that primary charging coil 54 and external telemetry coil 46 could also, in some circumstances be one and the same coil, a single coil essentially doing double duty as external telemetry coil 46 at some time and as primary charging coil 54 at another time.

Rechargeable power source 24 can be charged while implantable medical device 16 is in place in a patient through the use of external charging device 48. In an embodiment, external charging device 48 consists of charging unit 50 and external antenna 52. Charging unit 50 contains electronics 51 necessary to drive primary coil 54 with an oscillating current in order to induce current in secondary coil 34 when primary coil 54 is placed in the proximity, e.g., within twelve (12) inches (30.5 centimeters) of secondary coil 34. Electronics 51 may also determine an estimated time until a recharge session is complete. Charging unit 50 is operatively coupled to primary coil by cable 56. In an alternative embodiment, charging unit 50 and antenna 52 may be combined into a single unit. Antenna 52 may also optionally contain external telemetry coil 46 which may be operatively coupled to charging unit 50 if it is desired to communicate to or from implantable medical device 16 with external charging device 48. Alternatively, antenna 52 may optionally contain external telemetry coil 46 which can be operatively coupled to an external programming device, either individually or together with external charging unit 48. Alternatively, electronics may be located in or associated with implantable medical device 16, external charging device 48, a patient programmer, or a physician programmer, in various embodiments. Also alternatively, external charging device 48 and external antenna 52 may be located in the same device or unit. Further, it is also contemplated that external charging device 48, charging unit 50 or external antenna 52, or any or all of them, could be combined with a patient programmer and/or physician's programmer.

In an embodiment, repositionable magnetic core 58 may help to focus electromagnetic energy from primary coil 54 to more closely be aligned with secondary coil 34. Magnetic core 58 is completely optional. In an embodiment, magnetic core 58 is not used. In an embodiment, energy absorptive material 60 can help to absorb heat build-up in external antenna 52 which will also help allow for a lower temperature in implantable medical device 16 and/or help lower recharge times. In a further embodiment, thermally conductive material 62 is positioned covering at least a portion of the surface of external antenna 52 which contacts cutaneous boundary 38 of patient 18.

FIGS. 4-9 depict a series of screenshots from a display in external charging device 48 used for conveying information related to the charging of implantable medical device 16 to a user, such as patient 18. It is recognized that in alternative embodiments, the display could be associated with a physician programmer, a patient programmer, or any other external devices with componentry suitable to communicate with implantable medical device 16 and display the information described below. It is also to be recognized and understood that alternative forms of communicating information to patient, physician or other medical professional may take forms other than those explicitly illustrated herein. As an example, the display of a charge level, charge capacity or any time could be displayed as bar graphs, dots or LEDs, graphs, numerals or symbols. As another example, such information could also be communicated audibly, for example, beeps or a synthetic voice from a speaker associated with the implantable medical device, patient programmer, physician programmer or other allied device.

Figure 4:
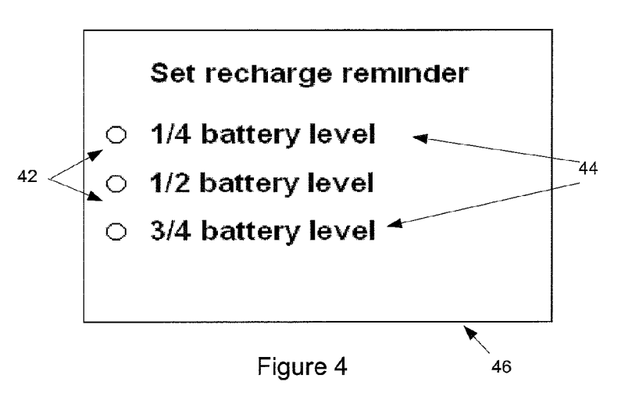
FIG. 4 shows a screen shot of a window for allowing a user to select when to receive a reminder to recharge their implantable medical device.

FIG. 4 shows a screenshot 46 allowing a user to program a reminder to conduct a recharge session when the charge on rechargeable power source 24 falls below a selected point. In an embodiment, the user may use radio buttons 42 choose one of several percentages 44 of rechargeable power source 24 capacity at which the reminder should be given. Which percentage 44 that may be chosen could depend on the needs of patient 18. For instance, where patient 18 was highly dependent on the therapy provided by implantable medical device 16, patient 18 may find it desirable to seek to ensure that rechargeable power source 24 not go below a relatively high percentage of total charge. Likewise, where patient 18 knows that access to external charging device 48 may become limited on short notice, such as where patient 18 is frequently compelled to be away from home for extended periods, it may be desirable to maintain rechargeable power source 24 at a high level of charge. By contrast, a patient 18 who knows there will be readily available access to external charging device 48, or whose therapy is not so highly critical that a temporary interruption would lead to significant discomfort or death, might avoid the relative inconvenience of having to recharge rechargeable power source 24 frequently in favor of allowing rechargeable power source 24 to discharge to a greater extent and thus recharge less frequently.

It is envisioned that reminders for recharging may be delivered to a patient based on a variety of different factors. In one alternative, a user may be allowed to enter a particular percentage level of charge at which the reminder is to be delivered. Alternatively, reminders may be delivered based not on the charge in rechargeable power source 24, but rather based on time elapsed since a previous recharging session, or based on a particular date or time.

Figure 5:
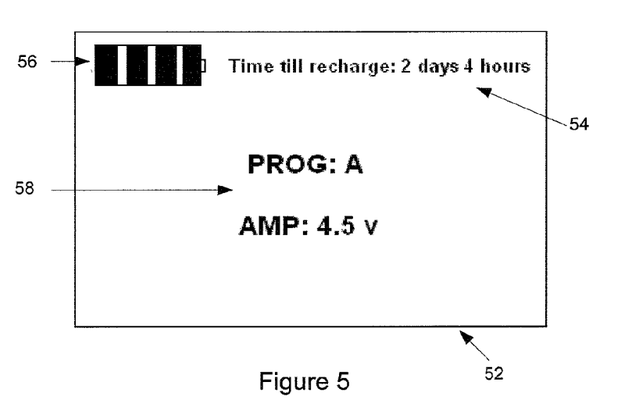
FIG. 5 shows a screen shot of a window for displaying an estimate of the time it will take to recharge an implantable medical device.

FIG. 5 shows a screenshot 52 that displays to a user the anticipated time 54 until recharge will be recommended. Included is a graphical representation 56 of the amount of charge left in rechargeable power source 24. In addition, information 58 pertaining to the operating parameters of implantable medical device 16 is displayed. In an embodiment, this information may include the pre-set program at which implantable medical device 16 is operating, and the voltage being delivered by rechargeable power source 24, though the display of other information is contemplated.

Figure 6:
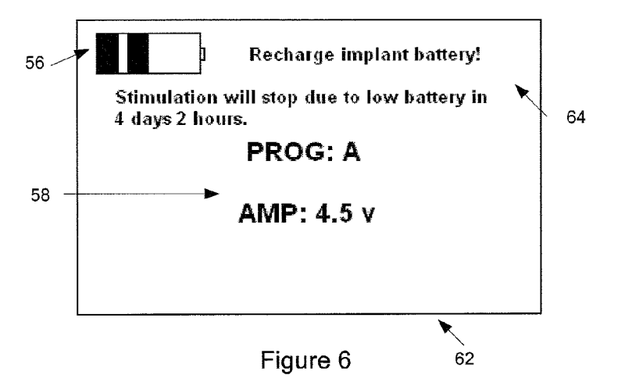
FIG. 6 shows a screen shot of a window for displaying a warning that the rechargeable power source of an implantable medical device is running low and an estimate of time before cessation of therapy is required if the implantable medical device is not recharge.

FIG. 6 shows a screenshot 62 that warns a user that the time has come to recharge rechargeable power source 24. Warnings 64 inform the user that rechargeable power source 24 needs to be recharged, and gives an estimate as to how much time remains before implantable medical device 16 will need to cease delivering therapy in order to conserve power. Graphical representation 56 shows approximately the amount of charge remaining in rechargeable power source 24; in this example, because the battery is depleted graphical representation 56 indicates less than full charge. Information 58 pertaining to the operating parameters of implantable medical device 16 is also displayed.

Figure 7:
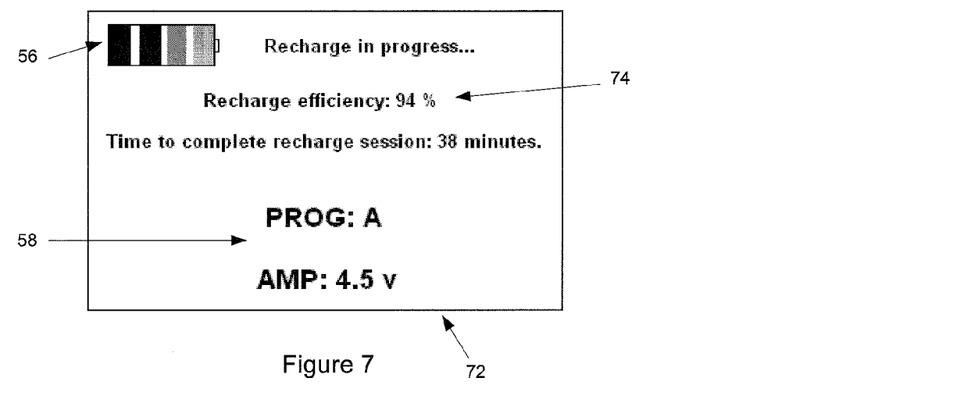
FIG. 7 shows a screen shot of a window for displaying information relating to a recharging session in progress.

FIG. 7 shows a screenshot 72 that provides a user with information relating to a recharging of rechargeable power source 24 while the recharging is in process. Information 74 pertaining to the recharging is displayed, including the efficiency of the connection between primary coil 54 and secondary coil 34, and the estimated time needed to complete the recharging (as determined in FIG. 10). Graphical representation 56 indicates both that the charge in rechargeable power supply 24 is less than full, due to the black bars not fully filling the outline of the battery, and that rechargeable power supply is receiving charge by depicting some bars as shaded, rather than either black or white. Information 58 pertaining to the operating parameters of implantable medical device 16 is also displayed.

Figure 8:
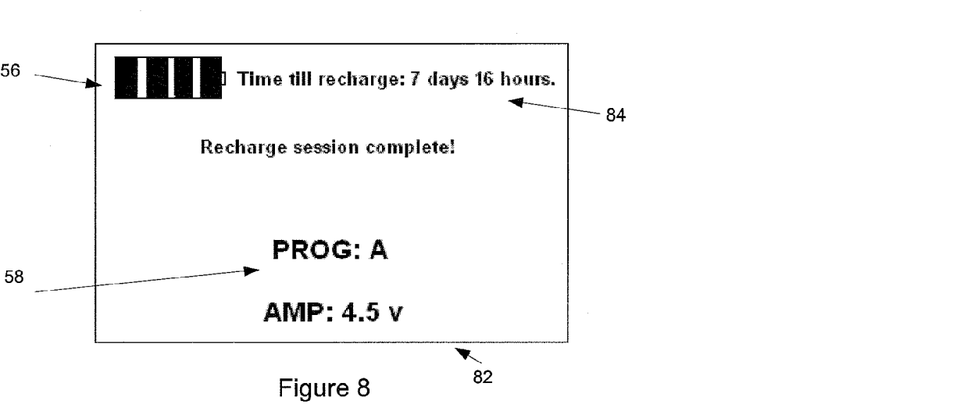
FIG. 8 shows a screen shot of a window for displaying information relating to expected time until recharge will again be required after a recharge has been completed.

FIG. 8 depicts a screenshot 82 that provides a user with information after a recharge session is complete. Information 84 pertaining to the completed recharging is displayed, including informing the user that the session is complete, as well as an estimate of the amount of time before the next recharging of rechargeable power supply 24 should occur. Graphical representation 56 indicates that the charging is complete by displaying a full battery symbol, while information 58 pertaining to the operating parameters of implantable medical device 16 is also displayed.

Figure 9:
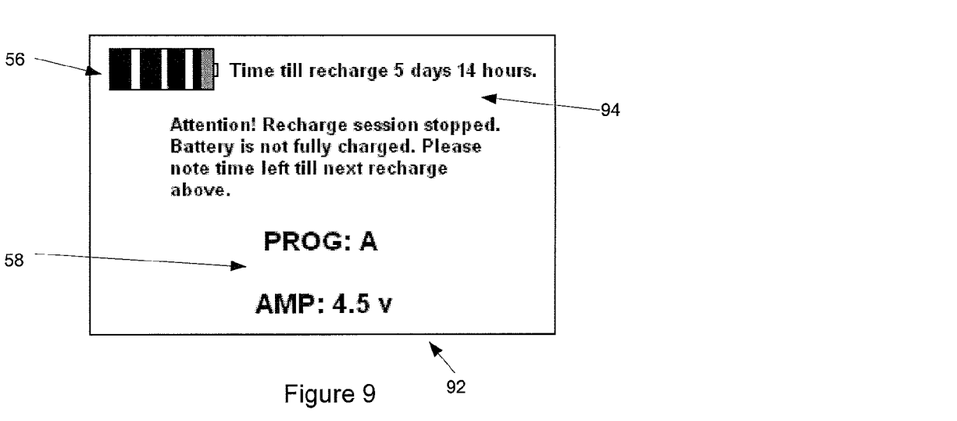
FIG. 9 shows a screen shot of a window for displaying information relating to expected time until recharge will again be required after a recharge session has been aborted before completion.

FIG. 9 shows a screenshot 92 that provides a user with information if the user cancels or aborts a recharge session before the recharge session has completed. In an alternative embodiment, screenshot 92 may be displayed if a user indicates an intention to abort or cancel a recharge session before the recharge session is complete. Information 94 informs the user that the recharge session has been stopped before rechargeable power source 24 has been completely charged, and informs the user as to the estimated time before another recharge session should be commenced. Graphical representation 56 indicates that rechargeable power supply 24 is not yet charged, while information 58 pertaining to the operating parameters of implantable medical device 16 is also displayed.

When external charging device 48 is utilized to recharge implantable medical device 16, external charging device 48 may first, before charging commences, estimate 110 (FIG. 10) an estimated time to complete recharging following the commencement of a recharge session using electronic componentry such as electronics 51. In alternative embodiments, the electronic componentry may be electronics 26 in implantable medical device 16, or may be electronics in other device operatively coupled to either implantable medical device 16 or external charging device 48, such as a patient programmer, a physician programmer, or other devices. A recharge session may be considered complete when the charge reaches a predetermined level. In an embodiment, the predetermined level may be when rechargeable power source is at least ninety percent (90%) fully charged. In an embodiment the estimate may also be displayed 111 to a user at this time.

Figure 10:
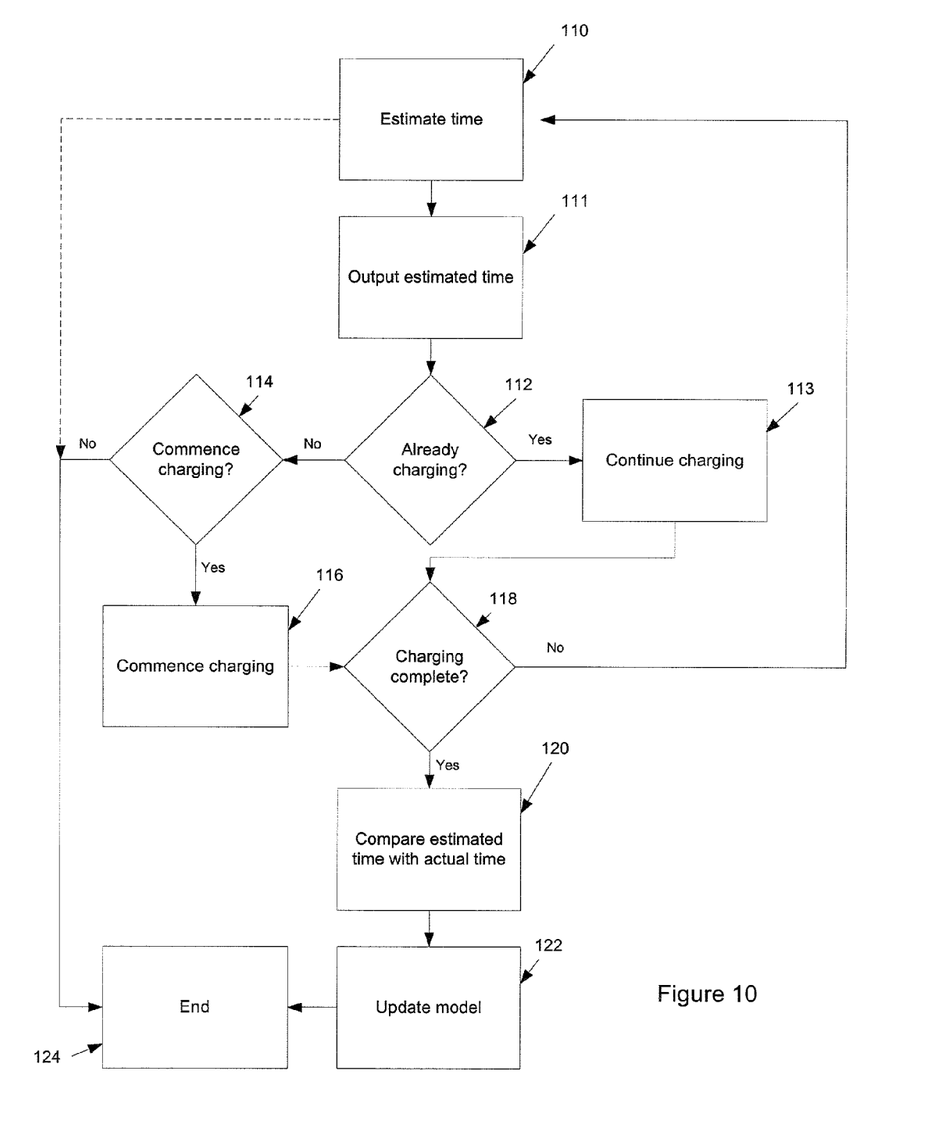
FIG. 10 is a flow chart for obtaining an estimate of a time to complete a recharge session, either as part of a recharging session, or from an external device not related to recharging.

If external charging device 48 is not already conducting a recharge session 112, external charging device 48 can prompt 114 the user whether to commence a recharge session. If the user selects to commence a session, charging begins. If not, external charging device 48 can end 124 further communication with the user. Where charging was already in process, charging continues 113. After some period of time, for example one minute, external charger can determine 118 whether rechargeable power source 24 has been fully charged and the charging session can end. If recharging is not complete then external charging device 48 can once again estimate 110 a time to complete recharging and, in an embodiment, display that estimate to the user. If recharging is complete then external charging device 48 can update the predetermined recharge model used to estimate 110 the time to complete recharging based on how accurate the initial estimate 110 was compared with the actual time to complete charging.

In an embodiment, an external device other than external charging device 48 may be used to obtain an estimate 110 of the time to recharge. Such an external device, while capable of operatively coupling to implantable medical device 16 would not be capable of charging rechargeable power source 24. Thus, after estimating 110 the time to recharge, the external device would display the estimated time and end 124 communication with the user. In various embodiments, the external device would be a handheld patient programmer or a physician programmer. In a further embodiment, the steps of estimating 110 the time until recharge are performed by electronics 26 of implantable medical device 16 instead of electronics 51 of external charging device 48, with the estimated time then transferred to external charging device 48 via coils 44, 46.

Figure 11:
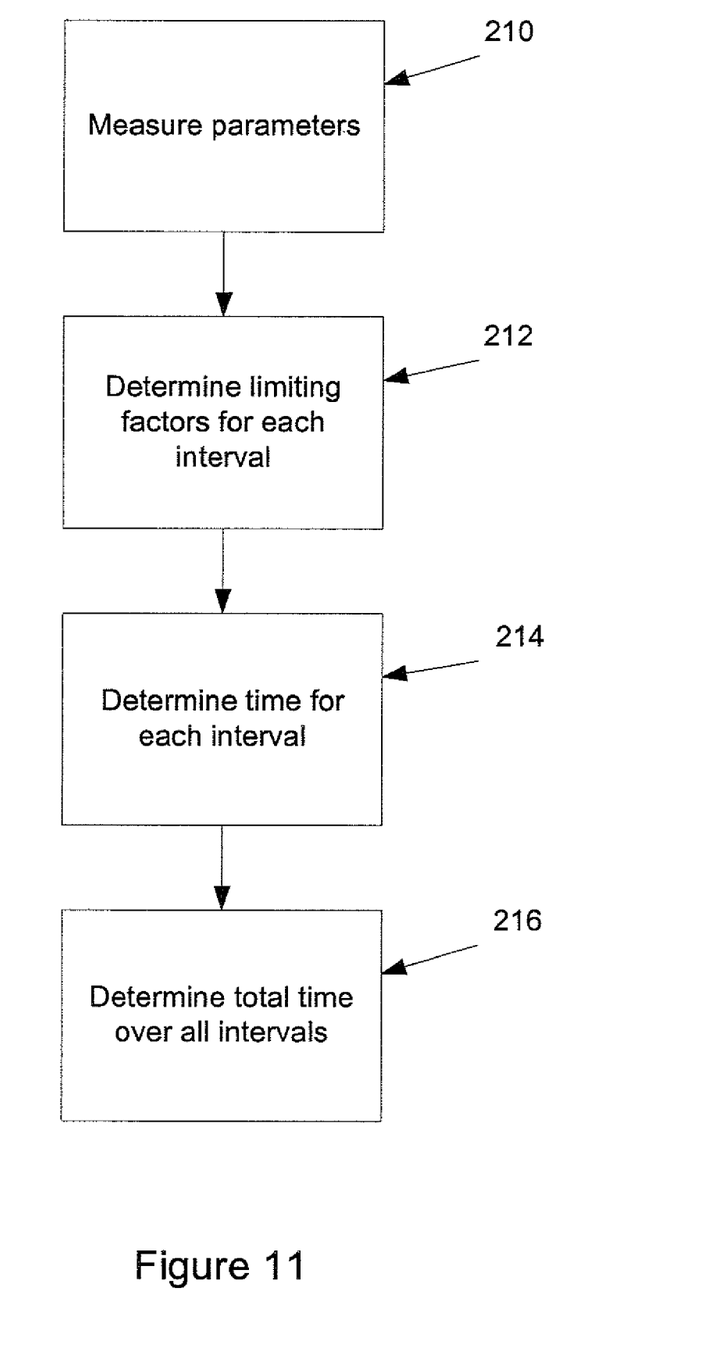
FIG. 11 is a flow chart for determining an estimate of a time to complete a recharge session.

In order to estimate 110 the time to recharge rechargeable power source 24, external charging device 48 first measures 210 a plurality of measured parameters relating to implantable medical device 16 and external charging device 48 (FIG. 11). Parameters that may be measured include: voltage over primary coil 54; current through primary coil 54; voltage over the power supply of charging unit 50; voltage over rechargeable power source 24; current through rechargeable power source 24; charge in rechargeable power source 24; voltage over secondary coil 34; current through secondary coil 34;

temperature of implantable medical device 16; temperature of external charging device 48, charging unit 50 and/or external antenna 52; where charging unit 50 is supplied by a battery, the charge stored in the battery may be measured; and where charging unit 50 is supplied by a battery, the charge capacity of the battery may be measured. Additional parameters may be measured, and listed parameters may not be measured, dependent on the characteristics of implantable medical device 16 and external charging device 48 being used.

Figure 12:
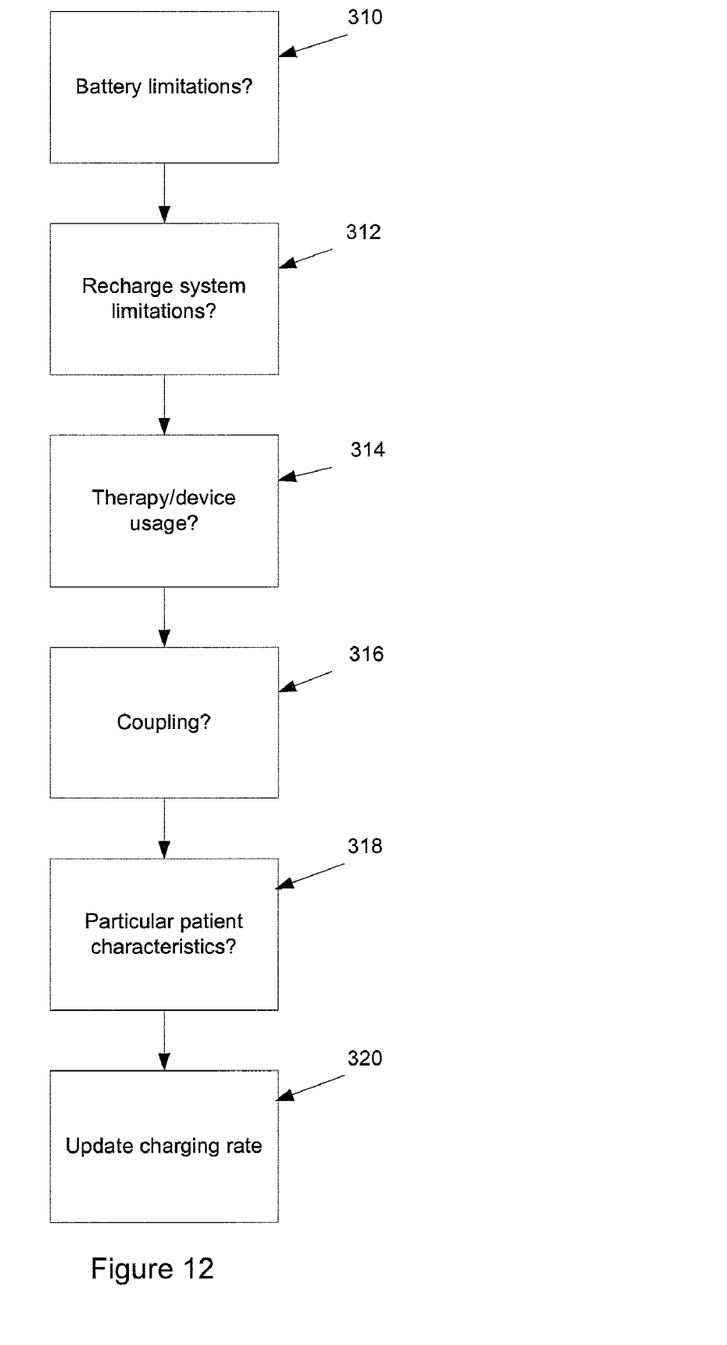
FIG. 12 is a flow chart for determining factors limiting the transfer of charge to an implantable medical device over various intervals of a recharging session.
Figure 13:
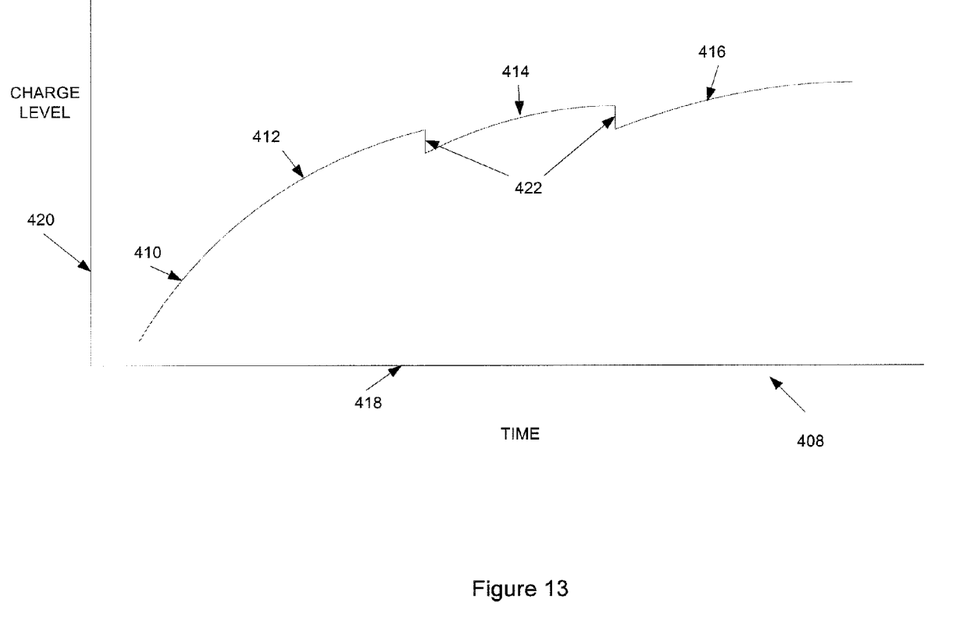
FIG. 13 is a graphical representation of a model used in estimating a time to complete a recharge session.

Once the parameters have been measured 210, external charging device 48 can determine 212, based on those parameters, a present limiting factor that limits how fast rechargeable power source 24 can safely be charged, as well as over remaining intervals of the recharge model (see FIGS. 12 and 13). Once the present limiting factor has been determined, if charging is currently proceeding, the rate at which charge is delivered can be adjusted to not exceed the determined limit. Then, external charging device 48 can determine 214, based on the determined limiting factors, how much time each interval in the model 408 will require to complete. Based on these individual calculations, external charging device 48 can then determine 216 a total estimated time to complete all intervals.

In order to determine the limiting factors based on the measured parameters, external charging device 48 may step through the known limiting factors for the combination of external charging device 48 and implantable medical device 16 being used (FIG. 12). An embodiment may first determine whether limitations of rechargeable power source 24 are controlling by checking 310 battery limitations. Voltage, current, charge level, known charge capacity and projected reduction in charge capacity as result of capacity fade in rechargeable power source 24 may be used to determine what percentage of the charge capacity is accounted for by the current charge level. Based on known models of rechargeable power source 24, external charging device 24 can determine what rate of charging rechargeable power source 24 can withstand without resultant damage; in an embodiment, the higher the percentage of charge level to charge capacity, the more desirable it is to deliver charge to rechargeable power source 24 slowly, as rapid influx of charge when the percentage is high is known to damage rechargeable power source 24.

It is envisioned that more than one type of external recharging device 24 may be used with any given type of implantable medical device 16. Though various types of external recharging device 24 may be similar, in an embodiment the different types may also have important differences in how they interact with implantable medical device 16. Thus, the limitations of the particular recharging system being utilized 312, comprised of implantable medical device 16 and external recharging unit 48, may limit how much charge may be delivered per unit time, taking into account, for example heat and temperature limitations. Interaction between primary coil 54 and secondary coil 34, as indicated by measured voltage and current over each, may limit the energy transfer rate. Likewise, in an embodiment external charging device 48 and implantable medical device 16 may each have a rectifier at the input of primary coil 54 or at the output of secondary coil 34, as the case may be, that may limit energy throughput. Additionally, because implantable medical device 16 may tend to gain heat during charging which, if it builds up too high, may cause discomfort or injury to patient 18, the energy transfer rate may have to be limited in order to prevent undue heating. Additionally, there may experience energy loss in tissue of patient 18, which also may cause discomfort or injury, and must be limited. Further, where external charging device 48 is powered from a battery source, the throughput of the battery may limit the ability to charge rechargeable power source 24, as may the capacity of the battery limit the total amount of energy that can be delivered.

In an embodiment, implantable medical device 16 can continue to deliver 314 therapy to patient 18 during the recharging session. Thus, implantable medical device 16 may continue to draw power from rechargeable power source 24 which may slow the rate at which rechargeable power source 24 experiences a net gain of charge. Factors such as power usage by therapy module 28 and electronics module 26 may slow recharging time.

The efficiency of the coupling between primary coil 54 and secondary coil 34 may create 316 another limiting factor. Unless the coils 34 and 54 are optimally aligned, the maximum rate of energy transfer between the two coils may be reduced by a factor corresponding, at least in part, to the degree to which the coils are out of optimal alignment. If coils 34 and 54 are brought too far out of alignment, the strength of the coupling between the two coils 34 and 54 can start to control the rate of energy transfer. The efficiency of coupling further may depend upon the size of primary coil 54 and secondary coil 34, the frequency used during charging and other factors.

Finally, based on updates to the model 408, it may be that, based on recharge history, behavior patterns of patient 18 will control 318 the projected rate of energy transfer. For instance, while coupling factor 316 may anticipate optimal or near-optimal coupling, external charging device 48 may have recorded that patient 18 chronically fails to attain optimal or near-optimal coupling. Thus, when estimating 110 time to complete charging, the model 408 may ultimately begin to adjust estimates base on patient history. Additionally, the model 408 may adjust for particular characteristics of implantable medical device 16 or external charging device 48, such as hardware characteristics, age and obsolescence. Finally, the charging rate may be updated 320 based on the results of previous analysis, factoring into consideration any changes to the limiting factor at any particular time.

When some or all of the above steps occur during the step of estimating time 110, charging may continue 113 at a new rate consistent with the results generated by model 408. The current through coil 54 may be altered to reflect the new rate. While adjustments will frequently be made to lower current through coil 54 when charging continues 113, it is envisioned that the current through coil 54 may be increased if the parameters of model 408 allow for doing so.

FIG. 13 depicts a graphical representation of model 408. Model 408 may be represented as a graph, as the graph is merely a visual representation of the various functions corresponding to the limiting factor that dominates at any given time. As each limiting factor is a separate function, the complete impact of all of the limiting factors may be represented graphically. X-axis 418 depicts time during a recharge session, and y-axis 420 depicts measured charge on rechargeable power source 24. Curve 410 thus depicts charge as a function of time. Transients 422 reflect the measured charge on the rechargeable power source 24 may, in an embodiment, be impossible to measure to a high degree of precision during charging, as the voltage over rechargeable power source 24 will be distorted by the charging process, and thus the measurement during charging will tend to be high, and will tend to change abruptly if the characteristics of the charging change. Model 408 depicts the process of charging Curve 410 is broken up into distinct intervals 412, 414, 416. Each interval corresponds to the change in the charging procedure anticipated as various factors limiting charging (see FIG. 12) become controlling as time passes and charge on rechargeable power source 24 accumulates. In an embodiment, unadjusted model 408 would have intervals corresponding to manufacturer projections for how recharging procedures would tend to progress. Thus, unadjusted, interval 412 may be limited by the inability of primary coil 54 and secondary coil 34 to couple beyond certain optimal or near-optimal levels, and thus would be limited by coupling 316. After a time, however, heat may begin to build up in implantable medical device 16 as a result of charging, and may begin to cause patient discomfort. At this point, recharge system limitations begin to control, and curve 410 transitions into interval 414. After some period of time of charging being limited by heating requirements, rechargeable power source 24 may have accumulated so much charge that the energy transfer rate must be slowed or risk damage to rechargeable power source 24 because of too much charge being transferred into too little remaining charge capacity. At this point, curve 410 transitions into interval 416. Note that for every interval 412, 414, 416, each possible limiting factor may determined, although only one limiting factor will actually be controlling.

The above sequence is illustrative only, and would tend to vary among various implantable medical devices 16 and various external charging devices 48. Further, as user conducts more recharge sessions, external charging device 48 will update model 408 to reflect actual recharge performance compared to the estimates. For instance, where coupling efficiency is consistently not what was anticipated in model 408, the projections for coupling efficiency 316 will be adjusted downward. Where model 408 originally projected coupling efficiency 316 to be controlling in an interval 412, 414, 416, curve 410 will be adjusted downward during that interval. Over intervals 412, 414, 416 where model 408 did not originally project coupling efficiency 316 would be controlling, coupling efficiency 316 may become controlling, and curve 410 would be adjusted downward over that interval 412, 414, 416. Over intervals 412, 414, 416 where coupling efficiency 316 is adjusted down, but does not become controlling, there would be no reflected change in curve 410.

In an embodiment, model 408 is adjusted based on an average performance of previous recharging sessions. Data pertaining to the recharge sessions are stored in memory either in implantable medical device 16 or external charging device 48, and incorporated into the performance averages. In an embodiment, adjustments are made based on the average of the previous ten recharging sessions. Thus, the previous ten results may be saved, and with each subsequent result the new one may be added and the oldest may be dropped. Then the ten results may be averaged together to compose the new functions represented in model 408, and the resulting graphical depiction would be altered. In an alternative embodiment, adjustments are made based on the average over the entire history of the device. Thus, in such an embodiment old results are never dropped from the computation of the average, as may occur in the embodiment described above. Measurements recorded are the same as those measured 210 as part of estimated the time to recharge (see FIG. 11).

Thus, embodiments of the time remaining to charge an implantable medical device, charger indicator, system and method therefore are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system, comprising:
an implantable medical device having a rechargeable power source, said rechargeable power source having a charge level and a charge capacity;
an external charger operatively coupled to said implantable medical device, said external charger having an external power source, said external charger charging said rechargeable power source;
electronic componentry determining an estimated time until said charge level reaches a predetermined level following commencement of a recharge session based on a plurality of measured parameters and a predetermined recharge model; and
a user output operatively coupled to said external charger and to said electronic componentry, outputting said time to a user;
wherein said predetermined recharge model is updated based on an actual time to recharge compared with said estimated time.

2. The system as in claim 1 wherein said external charger further comprises a primary coil, wherein said implantable medical device further comprises a secondary coil, and wherein said external charger operatively couples to said implantable medical device when said primary coil is placed in proximity of said secondary coil.

3. The system as in claim 2 wherein said plurality of measured parameters comprise at least one of: voltage over said primary coil; current through said primary coil; voltage over said external power source; voltage over said implantable power source; current through said implantable power source; voltage over said secondary coil; current through said secondary coil; temperature; charge stored in said external power source; charge capacity of said external power source; temperature of said external charger; and temperature of said implantable medical device.

4. The system as in claim 3 wherein said electronic componentry further determines a plurality of charging rates based on said plurality of measured parameters and said recharge model.

5. The system as in claim 4 wherein said predetermined recharge model has a plurality of intervals, each individual one of said plurality of intervals having an individual one of a plurality of limiting factors, said plurality of charging rates being based, at least in part, on at least one of said plurality of limiting factors.

6. The system as in claim 5 wherein said electronic componentry determines said time further based on said lowest individual one of said plurality of charging rates for each of said plurality of intervals.

7. The system as in claim 5 wherein said predetermined model is updated based, at least in part, on a change to said individual one of said plurality of limiting factors for at least one of said plurality of intervals.

8. The system as in claim 1 wherein said predetermined model is updated based, at least in part, on an average actual time to recharge of a plurality of recharge sessions.

9. A system, comprising:
an implantable medical device having a rechargeable power source, said rechargeable power source having a charge level and a charge capacity;
an external charger having:
an external power source operatively coupled to said implantable medical device and charging said rechargeable power source;
an electronic componentry determining an estimated time until said charge level reaches a predetermined level following commencement of a charge session by determining a plurality of charging rates based on a plurality of measured parameters and a predetermined recharge model, said predetermined recharging model having a plurality of intervals, each individual one of said plurality of intervals having an individual one of a plurality of limiting factors, said plurality of charging rates being based, at least in part, on at least one of said plurality of limiting factors, wherein said charging of said rechargeable power source occurs at a lowest individual one of said plurality of charging rates; and a user output operatively coupled to said external device and to said electronic componentry, outputting said time to a user;

wherein said predetermined recharge model is updated based on an actual time to recharge compared with said estimated time.

10. The system as in claim 9 wherein said external charger further comprises a primary coil, wherein said implantable medical device further comprises a secondary coil, and wherein said external charger operatively couples to said implantable medical device when said primary coil is placed in proximity of said secondary coil.

11. The system as in claim 10 wherein said plurality of measured parameters comprise at least one of: voltage over said primary coil; current through said primary coil; voltage over said external power source; voltage over said implantable power source; current through said implantable power source; voltage over said secondary coil; current through said secondary coil; temperature; charge stored in said external power source; charge capacity of said external power source; temperature of said external charger; and temperature of said implantable medical device.

* * * * *